US006331059B1

(12) United States Patent
Kudryashov et al.

(10) Patent No.: US 6,331,059 B1
(45) Date of Patent: Dec. 18, 2001

(54) HIGH RESOLUTION, MULTISPECTRAL, WIDE FIELD OF VIEW RETINAL IMAGER

(75) Inventors: Alexis Kudryashov; Andrey Viktorovich Larichev, both of Moscow (RU); Leonard John Otten, III, Placitas, NM (US)

(73) Assignee: Kestrel Corporation, Albuquerque, NM (US)

( * ) Notice: Subject to any disclaimer, the term of this patent is extended or adjusted under 35 U.S.C. 154(b) by 0 days.

(21) Appl. No.: 09/767,256

(22) Filed: Jan. 22, 2001

(51) Int. Cl.[7] .................................................. A61B 3/10
(52) U.S. Cl. .............................................................. 351/221
(58) Field of Search ................................... 351/205, 206, 351/211, 212, 219, 215, 216, 221, 246, 247; 600/108; 606/4, 5; 128/898

(56) References Cited

U.S. PATENT DOCUMENTS

| 5,892,569 | * | 4/1999 | Van De Velde | 351/221 |
| 5,949,521 | | 9/1999 | Williams et al. . | |
| 6,050,687 | | 4/2000 | Bille et al. . | |
| 6,199,986 | * | 3/2001 | Williams et al. | 351/221 |

OTHER PUBLICATIONS

M.C. Roggemann, et al., Linear reconstruction of compensated images: theory and experimental results, Applied Optics, vol. 31, No. 35, Dec. 10, 1992.

A. Kudryashov, et al., Bimorph Mirrors for Correction and Formation of Laser Beams, Proceedings of the 2nd International Workshop on Adaptive Optics for Industry and Medicine, Eidited by G.D. Love, University of Durham, England, Jul. 12–16, 1999.

J. Liang, et al., Supernormal vision and high–resolution retinal imaging through adaptive optics, J. Opt. Soc. Am. A, vol. 14, No. 11, Nov. 1997.

J. Liang, et al., Objective measurement of wave aberrations of the human eye with the use of a Hartmann–Shack wave–front sensor, J. Opt. Soc. Am. A, vol. 11, No. 7, Jul. 1994.

J. Liang, et al., Aberrations and retinal image quality of the normal human eye, J. Opt. Soc. Am. A, vol. 14, No. 11, Nov. 1997.

P. Artal, hartmann–Shack Wavefront Sensor in the Eye: Accuracy and Performance Limits, Proceedings of the 2nd International Workshop on Adaptive Optics for Industry and Medicine, edited by G.D. Love, University of Durham, England, Jul. 12–15, 1999.

L.D. Santana Haro, et al., Single vs. Symmetric and Asymmetric Double–pass measurement of the wavefront aberration of the Human Eye, Proceedings of the 2nd International Workshop on Adaptive Optics for Industry and Medicine, edited by G.D. Love, University of Durham, England, Jul. 12–15, 1999.

(List continued on next page.)

*Primary Examiner*—George Manuel
(74) *Attorney, Agent, or Firm*—DeWitt M. Morgan

(57) ABSTRACT

An ophthalmic instrument (for obtaining high resolution, wide field of area multi-spectral retinal images) including a fundus retinal imager, (which includes optics for illuminating and imaging the retina of the eye); apparatus for generating a reference beam coupled to the fundus optics to form a reference area on the retina; a wavefront sensor optically coupled to the fundus optics for measuring the wavefront produced by optical aberrations within the eye and the imager optics; wavefront compensation optics coupled to the fundus optics for correcting large, low order aberrations in the wavefront; a high resolution detector optically coupled to the imager optics and the wavefront compensation optics; and a computer (which is connected to the wavefront sensor, the wavefront compensation optics, and the high resolution camera) including an algorithm for correcting, small, high order aberrations on the wavefront and residual low order aberrations.

32 Claims, 11 Drawing Sheets

OTHER PUBLICATIONS

A. Baca, WaveFront Sciences takes the eye's measure, Albuquerque Journal Business Outlook, Jun. 8, 2000.

M.C. Rogemann, et al., Image reconstruction by means of wave–front sensor measurments in closed–loop adaptive–optics systems, J. Opt. Soc. Am. A, vol. 10, No. 9, Sep. 1993.

M.C. Roggemann, Limited degree–of–freedom adaptive optics and image reconstruction, Applied Optics, vol. 30, No. 29, Oct. 10, 1991.

J. Primot, et al., Deconvolution from wave–front sensing: a new technique for compensating turbulence degraded images, J. Opt. Soc. Am. A, vol. 7, No. 9, Sep. 1990.

A. Larichev oral presentation: Deconvolution of Color Retinal Images with Wavefront Sensing, at Cohference on Domain Optical Methods in Biomedical Science and Clinical Applications V, Amsterdam, the Netherlands, 2000.

* cited by examiner

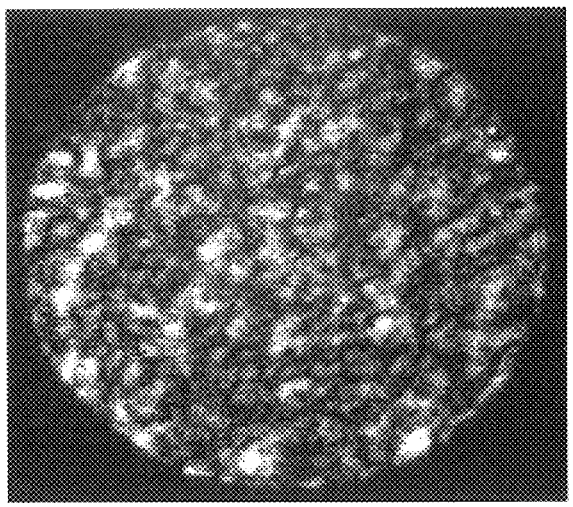 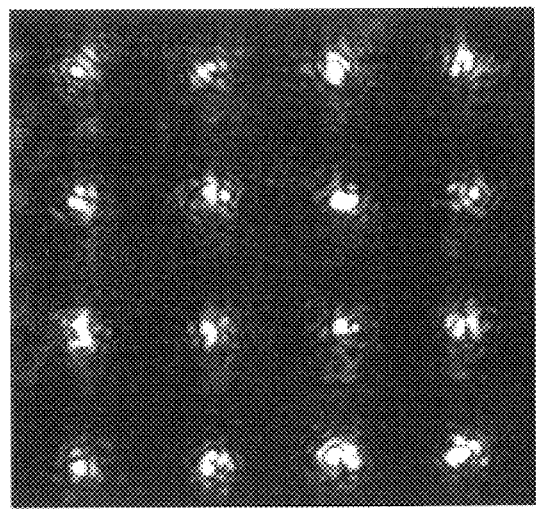
Intensity distribution within the eye pupil and corresponding hartmanogram with fixed source.
Figure 4A                                        Figure 4B Intensity distribution within the eye pupil and corresponding hartmanogram with scanning source.

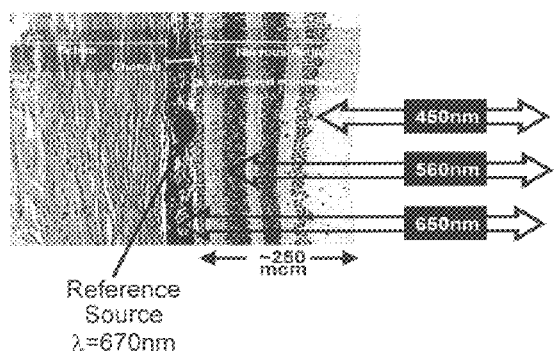
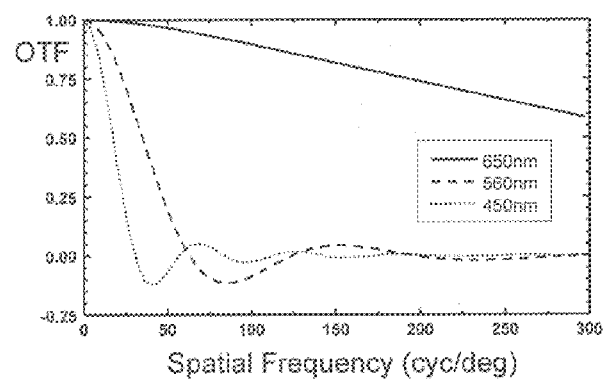
Figure 6A
Figure 6B

|  | Prior Art | Instrument 11 |
|---|---|---|
| FOV | 1 degree | Up to 20 degrees |
| Imaging cycle (loop) | 10 - 20 | 1 |
| Images per loop | 6 | 1 |
| Duration per image | 300 ms | < 30 ms |
| Image registration | Required | Not required |
| S-H Lenslets | 217 | 80 |
| Number of Actuators | 37 | 18 |
| Image deconvolution | None | Depth Sensitive Convolution |
| Effects of scatter | Adds a Degradation | Compensated For |
| Reduce speckle effects | Use Multiple Images | Dithered Reference |
| Chromatic Aberration | Unknown | Corrected |
| Reference | Fixed | Moving |
| Spatial Resolution | ~10 micrometers | ~1 micrometer |
| Number of Spectral Bands | Panchromatic | Up to 10 |
| Adaptive Optics Mirror | Individual Actuators | BiMorph |

Figure 11

HIGH RESOLUTION, MULTISPECTRAL, WIDE FIELD OF VIEW RETINAL IMAGER

FIELD OF THE INVENTION

The present invention is directed to an improved fundus retinal imaging system which provides high resolution multispectral retinal images over a wide field of view to permit early diagnosis of various pathologies such as diabetic retinopathy, ARMD (age related malocular degeneration) and glaucoma. More specifically, the present invention relates to a conventional fundus retinal imager combined with, inter alia, a multispectral source, a dithered reference, a wavefront sensor, a deformable mirror, a high resolution camera and deconvoluting software to produce wide field, high resolution, multispectral images of the retina.

BACKGROUND OF THE INVENTION

The ability to resolve fine details on retinal images can play a key role in the early diagnosis of vision loss. Certain biochemical and cellular-scale features, which may be present in the early stages of many retinal diseases (e.g., ARMD), cannot be detected today with current funduscopic instruments because of the losses in spatial resolution introduced by the ocular medium of the eye and the lack of selectable spectral data. Additionally, the presence of aberrations within the eye limits the effective input pupil size of a standard fundus retinal imager to about 2 mm. This limit leads to a decrease in the contrast of the small image details due to diffraction effects.

A partial solution to the foregoing problems is to use an adaptive optical system, first for measuring aberrations and then for correcting such aberrations. With such a system, it is possible to increase the system pupil diameter up to 7–8 mm and achieve a resolution on the order of 10 $\mu$m. The feasibility of this approach has been demonstrated recently by J. Liang et al., "Supernormal vision and high-resolution retinal imaging, through adaptive optics," J. Opt. Soc. Am. A/Vol. 14, No. 11/November, 1997. They report constructing a fundus retinal imager equipped with adaptive optics that permits the imaging of microscopic structures in living human retinas. The optical system, which is illustrated in FIG. 2 of this reference, includes a deformable mirror for wavefront compensation and a wavefront sensing module including a Hartmann-Shack (also known as a Shack-Hartmann; hereinafter abbreviated "S-H") wavefront sensor. Collectively, the S-H sensor, (which is used to measure the eye's optical aberrations) and the deformable mirror (which is used to make small corrections of the optical aberrations) is sometimes referred to as an adaptive optics system. The deformable mirror is positioned in a plane which is conjugate with both the eye's pupil plane and the front surface of the lenslet array of the S-H wavefront sensor. The S-H wavefront sensor is described in detail in J. Liang, et al., "Objective measurement of wave aberrations of the human eye with the use of a Hartman-Shack wave-front sensor," J. Opt. Soc. Am./Vol. 11, No. 7/July 1994. The displacement of the image, of each of the lenslets in the S-H wave front sensor, on a CCD gives information required to estimate the local wavefront slope. From the array of slopes, the wavefront is reconstructed via a least squares technique into Zernike modes. In operation, a point source produced on the retina by a laser beam is reflected from the retina and received by the lenslet array of the S-H wavefront sensor such that each of the lenslets forms an image of the retinal point source in the focal plane the CCD detector located adjacent to the lenslet array. The output signal from the CCD detector is acquired by a computer, which processes the signal and produces correction signals which, via a feedback loop, are used to control the deformable mirror.

There are a number of limitations associated with the above described instrumentation including:
1. Sensitively to speckle modulation within the eye;
2. The deformable mirror can only provide limited correction;
3. It is a panchromatic instrument, not multispectral;
4. It operates with a limited field of view, on the order of 2–5 degrees; and
5. Several renditions of the S-H output are required to estimate the wavefront.

Further, while it is claimed that it is useful in determining aberrations beyond defocus and astigmatism and providing improved imaging inside of the eye, there is no discussion of its use as a clinical instrument to be used in the diagnosis of the major causes of vision loss and blindness. Finally, the Liang et al. instrument is a laboratory device composed of very expensive one-of-a-kind components.

OBJECTS OF THE INVENTION

It is an object of the present invention to provide, in association with any commercially available fundus imager, an improved, low bandwidth adaptive optics system and an optimized depth sensitive deconvolution technique to increase retinal imaging resolution and field of view, to thereby enable a clinical device to improve the level of opthmological healthcare.

It is another object of the present invention to provide a deconvolution technique which takes into account the reflectance of difficult colors from the various layers of the retina to provide a high spatial resolution, multi-spectral image over a wide field of view.

It is another object of the present invention to provide a fundus based opthalmic instrument which has resolution at the micron level (i.e., less than the size of a cell).

It is yet another object of the present invention to provide a retinal imaging system which uses a scanning (or dithered) reference spot to mitigate the speckle problems associated with the instrumentation disclosed by Liang et al. and which allows wavefront estimates and images of the retina to be taken with one exposure instead of multiple exposures.

It is yet another object of the present invention to correct for large, low order aberrations (e.g., tip, tilt, focus, and astigmatism) using a bimorph adaptive optical element.

It is yet still another object of the present invention to use post image depth sensitive deconvolution techniques to correct for high order aberrations (e.g., coma, trifocal, spherical, and higher terms) and remove residual low order aberrations.

It is yet a further object of the present invention to provide the foregoing in an affordable attachment to existing fundus retinal imagers.

The foregoing and other objects will be apparent from the disclosure which follows.

SUMMARY OF THE INVENTION

An ophthalmic instrument having a wide field of view (up to 20 degrees) including a retinal imager, (which includes optics for illuminating and imaging the retina of the eye); apparatus for generating a reference beam coupled to the imager optics to form a reference area on the retina; a wavefront sensor optically coupled to the imager optics for measuring the wavefront produced by optical aberrations within the eye and the imager optics; wavefront compensation optics coupled to the imager optics for correcting large, low order aberrations in the wavefront; a high resolution detector optically coupled to the imager optics and the wavefront compensation optics; and a computer (which is connected to the wavefront sensor, the wavefront compensation optics, and the high resolution camera) including an algorithm for correcting, small, high order aberrations on the wavefront and residual low order aberrations. The wavefront sensor includes a Shack-Hartmann wavefront sensor having a lenslet array and a detector positioned in the front surface of the lenslet array for producing a Hartmannogram. The computer includes means for estimating the wavefront from the Hartmannogram and sending a correction signal to the wavefront compensation optics to correct large, low order aberrations in the wavefront. Only one Hartmannogram is required, thereby reducing the exposure of the retina to the spot, and avoiding the need to register successive Hartmannograms. The wavefront compensation optics includes a deformable mirror, such as a bimoph mirror. The algorithm for correcting small, high order aberrations includes a deconvolution algorithm which utilizes information from both the wavefront sensor and the high resolution detector. The deconvolution algorithm includes an algorithm for estimating the wavefront sensed by the wavefront sensor, means for estimating the Optical Transfer Function of the wavefront, and Weiner Filter Estimation means. The deconvolution algorithm also includes image reconstruction algorithms. The instrument also includes a plurality of filters and the deconvolution algorithm also accounts for the reflectance of various wavelengths of light from different depths within the retina to produce a multispectral deconvoluted image of the retina. The instrument also includes a mechanism for dithering the reference beam, including a rotatable wedge. Because the instrument produces a wide field of view, a large format, high resolution detector is required. The instrument, less the retinal imager, is an adaptive optics system which can be used in association with a number of commercial imagers, including fundus imagers.

A method of obtaining high resolution, wide field of view, multispectral images of the retina from the apparatus of the present invention.

These and other objects will be evident from the description that follows.

BRIEF DESCRIPTION OF THE DRAWINGS

FIG. 4A is an illustration of the intensity distribution within a pupil plane of the eye produced by an unscanned reference beam;

FIG. 4B is the corresponding Hartmannogram produced by an unscanned reference beam;

FIG. 6A shows the layers of the retina where various wavelengths of light are reflected;

FIG. 6B is a graph showing the OTF (Optical Transfer Function) of the eye vs. Spatial Frequency for light in the range of, respectively, 650 nm, 560 nm and 450 nm;

FIG. 11 is a table comparing the features achieved by the present invention with the prior art.

DESCRIPTION OF THE PREFERRED EMBODIMENT

Figure 1:
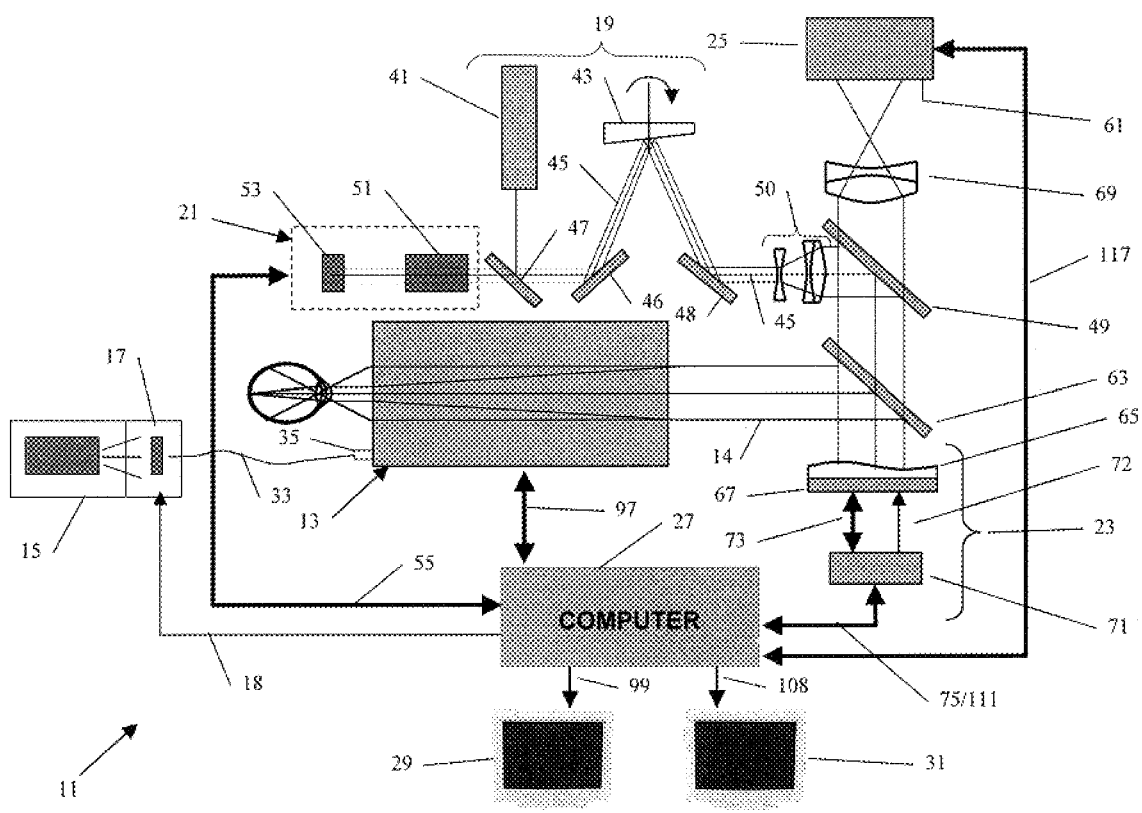
FIG. 1 is a partial block diagram/partial optical schematic of the present invention, including a fundus imager.

With reference to FIG. 1, improved retinal imaging system 11 includes fundus retinal imager 13, light source 15, filter assembly 17, dithered reference source generator 19, wavefront sensor 21, deformable mirror assembly 23, large format, high resolution detector 25, computer 27 and monitors 29 and 31.

In the present embodiment, fundus retinal imager 13 is a JST ZOMZ, Model KFG3 which provides collimated output 14. However, as those skilled in the art will appreciate other fundus imagers such as the Zeiss FF4 or FF5, the Topcon TRC-50 series or the Canon CF-60 series or CR5-45 can also be used. Light source 15 and filter assembly 17 are connected to fundus retinal imager 13 via fiber optic cable 33 and the standard fiber optic port 35 provided on fundus retinal imager 13. Source 15 includes an illumination lamp such as a tungston, xenon or metal halide lamp (not shown). Filter assembly 17, which is controlled by computer 27 via control line is, includes up to 10 filters for use in creating multispectral images. Fundus retinal imager 13 includes UV and IR blocking filters (not shown). Filter assembly 17 also includes (a) mechanism(s) (not shown) for selectively positioning a particular filter in the optical path between source 17 and fiber optic cable 33.

Dithered reference source generator 19 (which is controlled by computer 27 by a control line (not shown)) includes a source 41 of collimated laser light having, for example, a wavelength of 670 nm (to form a reference spot on the back of the retina) and a rotating wedge 43 for scanning (or dithering) the beam 45 from source 41. Wedge 43 is a mirrored wedge whose wedge angle is used to set the desired dithered spot area. The speed of rotation, which is adjustable, is determined by the exposure time of wavefront sensor 21 and the power of source 41. Collimated beam 45 is first reflected by beam splitter 47 and then by mirror 46 to wedge 43. Beam 45 is then optically connected to the optical system (not shown) of fundus retinal imager 13 via mirror 48, beam expanding optics 50, and beam splitters 49 and 63. The internal optical system of fundus retinal imager 13 (not shown) focuses beam 45 into the back surface of the retina of the eye being examined.

Wavefront sensor 21 includes a S-H lenslet array 51 and a CCD detector 53, the image plane of which is positioned in the focal plane of array 51. Wavefront sensor 21 is connected to computer 27 via control and data cable 5 5. Detector 53 is a commercially available low noise sensor (e.g. a Hitachi KP-F2A).

The image plane of high-resolution detector 25 is placed in the image plane 61 of fundus retinal imager 13. The two are optically coupled by beam splitters 63 and 49, mirrored, deformable surface 65 of adaptive optics mirror 67, and imaging lens 69. Adaptive optics mirror 67 is electrically connected to wavefront sensor electronic drivers 71 via power cable 72 and control cable 73. In turn, electronic drivers 71 is connected to computer 27 via cable 75. Deformable mirror assembly 23, including adaptive optics mirror 67 (which is a bimorph mirror) is described in A. Kudryashov et al., "Bimorph Mirrors for Correction and Formation of Laser Beams," Proceedings of the $2^{nd}$ nd International Workshop on Adaptive Optics for Industry and Medicine, World Scientific, pp.193–199. Preferably, detector 25 is a full-frame, large format CCD image sensor such as the Electron CFK-3020 incorporating an FTF 3020-M (Phillips) detector having 3072(H)×2048(V) active pixels. The large format is necessary because the field of view produced by the wavefront sensor 21, adaptive optics 23, and fundus retinal imager 13 are capable of providing up to 20 degrees.

Figure 2:
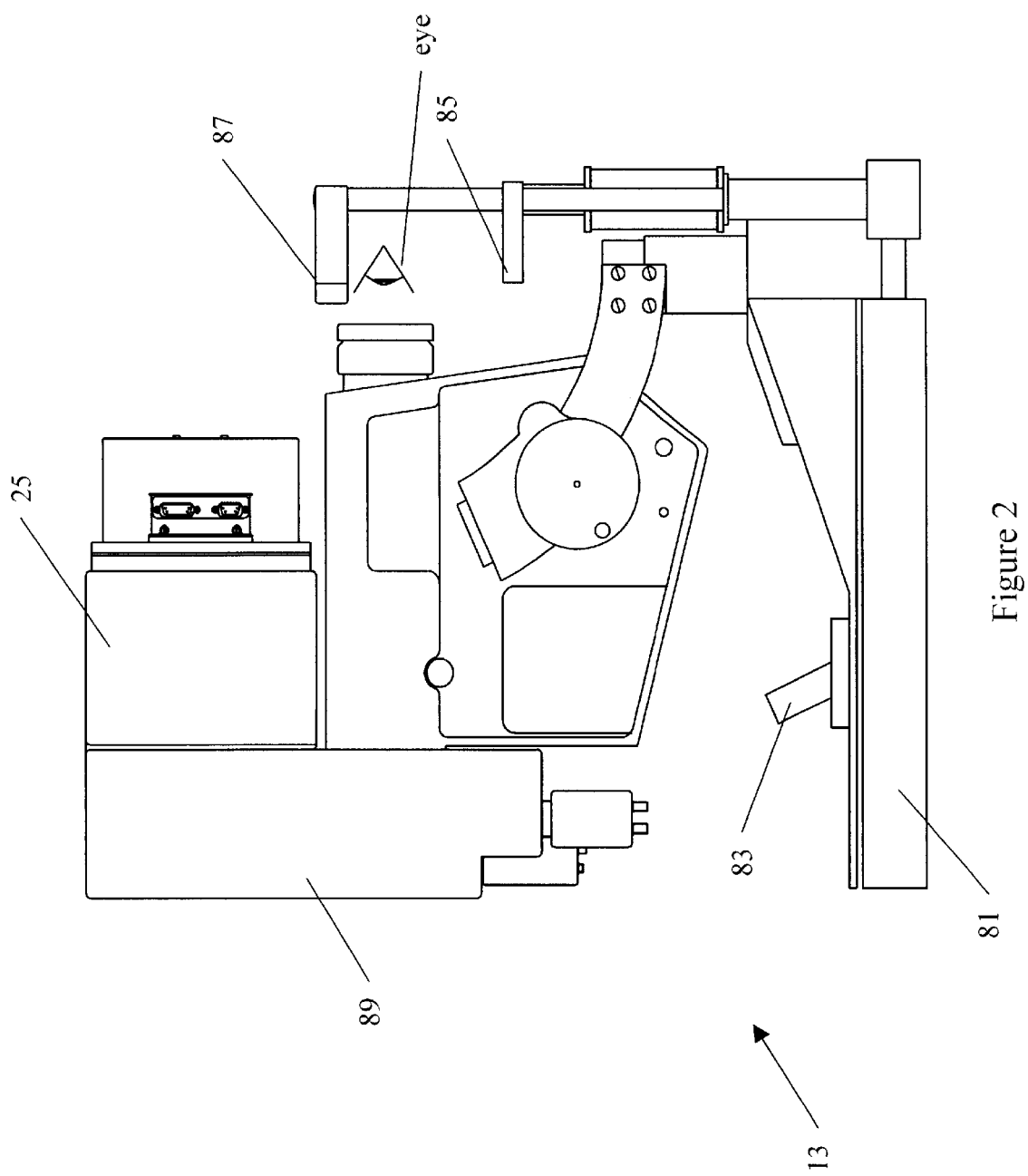
FIG. 2 is a side elevation showing a conventional fundus retinal imager in association with, for instance, the housings for the improved adaptive optics and high resolution camera of the present invention.

With reference to FIG. 2, fundus retinal imager 13 includes a base 81, joystick control 83 for aligning the optics (not shown) with the eye of a patient. Fundus retinal imager 13 also includes a chin rest 85 and a forehead rest 87. The adaptive optics of the present invention (i.e., wavefront sensor 21 and deformable mirror assembly 23) and high resolution detector 25 are supported in housing 89.

Figure 3:
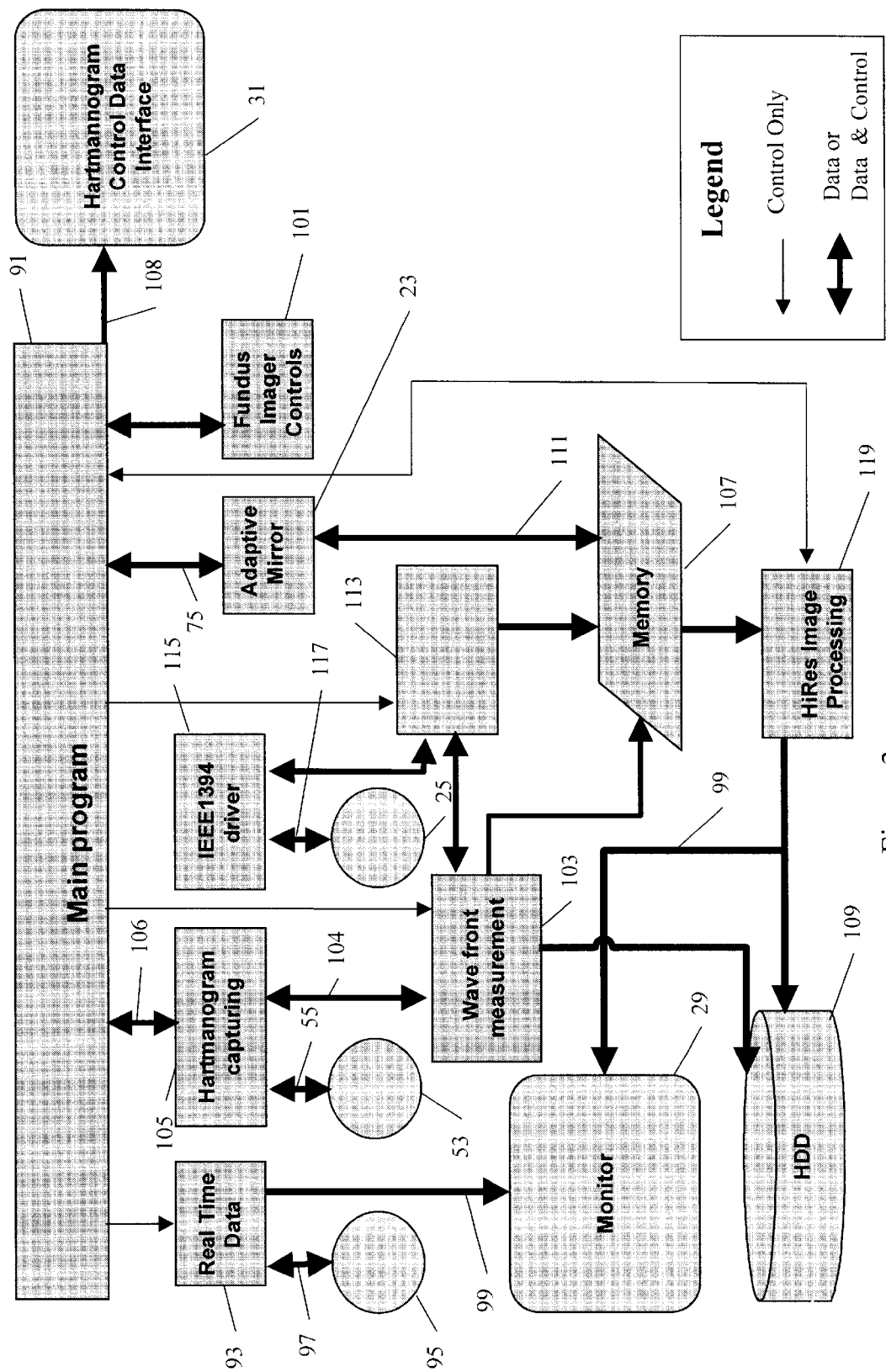
FIG. 3 is a schematic diagram illustrating the principal software controls and data flow of the present invention.

The overall operation of the hardware and software of retinal imaging system 11, is best described with reference to FIG. 3. Main program 91 operates a number of subroutines and hardware to control the various functions of the system including frame grabing, the storage (both temporarily and permanently) of data, and the processing of imagery. Data interface 93, which is turned on and run by main program 91, is used to supply live images of the retina to monitor 29 from CCD detector 95 (e.g. a JAI CV-M50 IR), which is running continuously, and which is part of fundus retinal imager 13). Detector 95 is connected to computer 27 by data and control cable 97. Computer 27 is connected to monitor 29 via data cable 99. Subroutine 101 runs the balance of the fundus imager's electronics (e.g. illumination controls, target fixation controls). Subroutine 103, which is controlled by program 91, includes a conventional algorithm for wavefront estimation based on the centroids contained in the Hartmannogram, and a conventional algorithm for converting the physical description of the wavefront to the commands used to control adaptive optics mirror 67 (to alter the slope of deformable surface 65) and estimating the Optical Transfer Function used in the deconvolution calculations discussed below. Detector 53, which is also continuously running, sends Hartmannograms to computer 27 via data and control lines 55 and 104. Subroutine 103 also controls data interface 105, sends wavefront data to memory 107 (for temporary storage) and wavefront data to hard drive 109 (for permanent storage). Main program 91 also sends data, via control and data line 75/111, to electronic drivers 71 for changing the contour of deformable surface 65 using data from memory 107. Finally, program 91 controls high resolution image subroutine 113 which, in turn, controls data interface 115 (or equivalent), which grabs images off high resolution CCD detector 25 via control and data cable 117. Image data is transferred from detector interface 115 to subroutine 113 which, after processing as explained below, is transferred to memory 107. While the foregoing has referenced data interfaces 93, 105 and 115, those skilled in the art will appreciate that alternate hardware/software combinations, such as a frame graber, can be used to capture the respective images from detectors 25, 53 and 91.

A major problem with the prior art has been the speckle-like reflection of the laser light reference beam from the retina. Without dithering the resulting image of the pupil plane on detector 53 of wavefront sensor 21 is highly scintillated. FIG. 4A illustrates the speckle-like pattern that the human eye creates. FIG. 4B illustrates the corresponding Hartmannogram. As is apparent from this latter figure, the shape of the spots on the Hartmannogram is highly irregular. This, in turn, makes determination of the centroids of the spot's centers difficult which, in turn, greatly reduces the accuracy of the wavefront estimation.

Figure 5A:
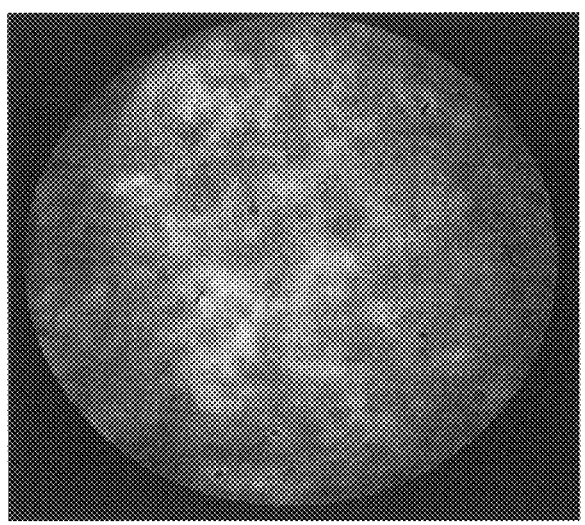
FIG. 5A illustrates the intensity distribution within a pupil plane of the eye produced by the dithered reference beam of the present invention.
Figure 5B:
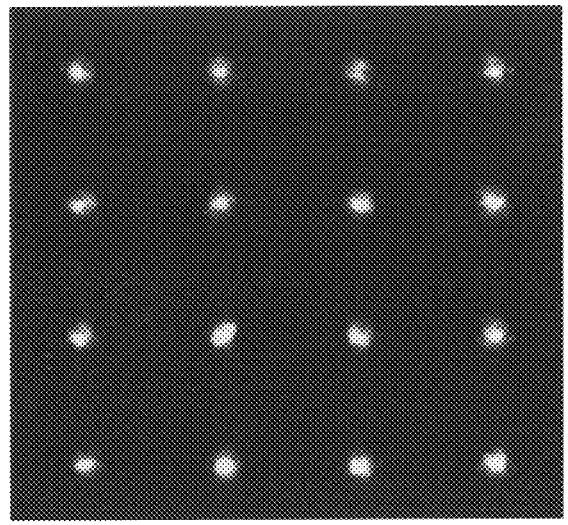
FIG. 5B is the corresponding Hartmannogram produced by the dithered reference beam of the present invention.

To overcome this problem retinal imaging system 11 incorporates a novel dithered reference source generator 19, which scans reference beam 45 over a small patch of the retina. In the present embodiment the scanning patch is 200–300 µm in diameter. Wedge 43 has a scanning speed of 50–100 Hz. The results achieved are illustrated in FIG. 5A, which is an image of the same human eye used in the generation of the image illustrated in FIG. 4A, but taken with mirrored wedge 43 operating. With the foregoing scanning rate, during the integration time of CCD detector 53 (i.e., 30 ms), the speckle pattern is much improved. Consequently, the intensity modulation within the pupil plane of the wavefront sensor becomes much smaller. The spots on the resulting Hartmannogram, illustrated in FIG. 5B, became more regular (e.g., Gaussian like). This results in an increase in the accuracy of the wavefront estimation of, approximately, 20 times that achieved by the prior art. Additionally, the time necessary to correct the aberrations in the eye is considerably reduced, resulting in less exposure of the retina to the laser reference beam. And, because with instrument 11 only one Hartmannogram is necessary, as opposed to the multiple Hartmannograms required by the prior art adaptive optics, the necessity of registering a series of successive Hartmannogram images (which requires a considerable amount of processing time) and the inaccuracies inherent in such registering is avoided. (Registration is necessary with the prior art because the eye shifts slightly between successive images due to sacades, an involuntary motion of the eye.

Figure 7:
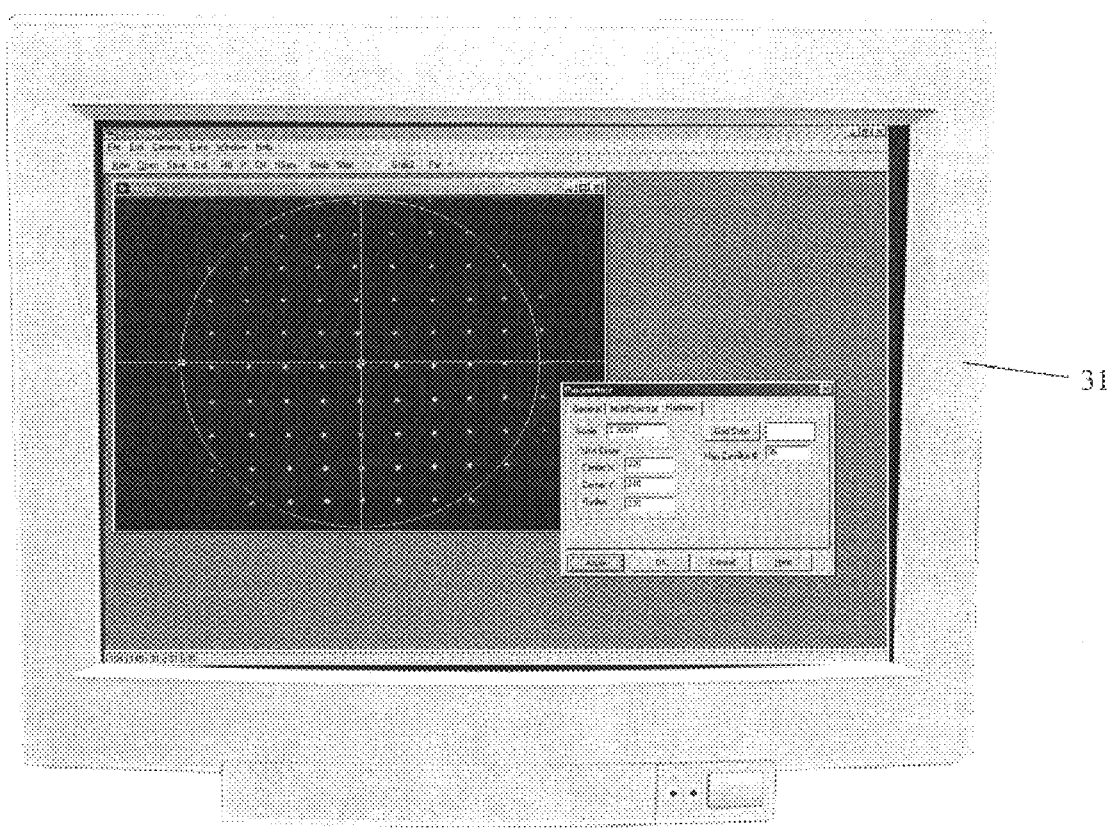
FIG. 7 is a sample view from one of the monitors incorporated in the preferred embodiment of the present invention, showing the Hartmannogram and a setting used to operate the wavefront sensor.

In operation, after the patient's eye has been dilated, the patient's head is properly positioned by chin rest 85 and brow rest 87 so that the patient's eye is properly aligned with the optical axis (not shown) of fundus retinal imager 13. This is determined by viewing the live, real time, video data from CCD 95 on monitor 29. Once proper alignment is achieved, laser 41 is energized through use of a shutter (not shown), so that dithered reference beam 45 is placed on the retina of the eye being examined. Through the use of, inter alia, controls 101, the existing internal optics of the fundus retinal imager 13 are used to focus the dithered reference beam on the retina. The use of a long wavelength visible band laser (e.g., 670 nm) places the focus at the back of the retina, as illustrated in FIG. 6A. The reference beam is reflected off the back of the retina and is reflected by beam splitters 49 and 47 to lenslet array 51 of S-H sensor 21. The resulting Hartmannogram is recorded by CCD detector 53 and transferred to data interface 105 by cable 55. The image data is then transferred to and processed by subroutine 103, where the wavefront is estimated, including calculation of the optical transfer function (OTF). As is illustrated in FIG. 3, image data is transmitted to both memory 107 (for temporary storage) and hard drive 109 (for permanent storage). In turn, data is transmitted from memory 107 to electronic drivers 71, via control and data line 111, to modify the curvature of surface 65 of bimorph mirror 67, to apply a conjugate wavefront to the image of the retina relayed from fundus retinal imager 13 to high resolution CCD detector 25 (as explained in further detail below). Via main program 91, data interface 105, data line 106, and data line 108 the Hartmannogram may be viewed on the screen of monitor 31, as illustrated in FIG. 7. Operating parameters for wavefront sensor 21 and data interface 105 are also displayed on monitor 31.

Figure 8:
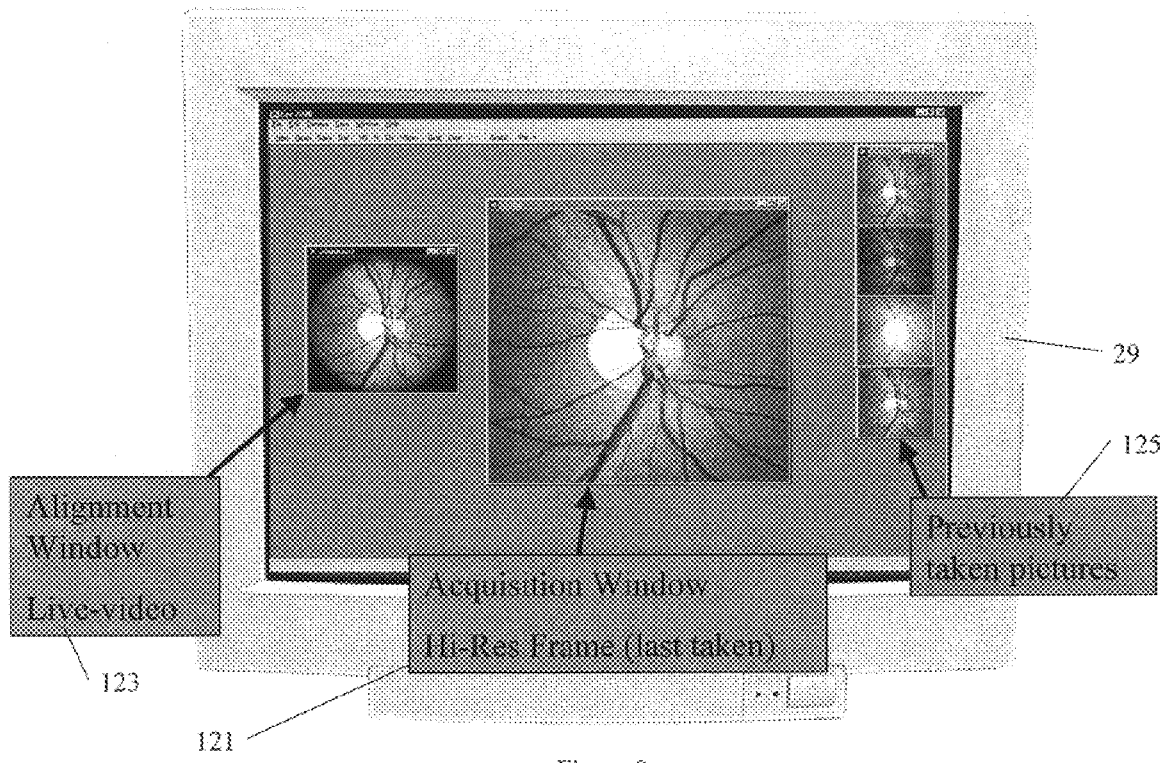
FIG. 8 is a view of a sample screen from the other of the monitors incorporated in the preferred embodiment of the present invention, showing the type of imagery used to align the fundus retinal imager and the imagery obtained from the high resolution detector.

To capture an image of the retina being examined, the retina is illuminated with white or filtered light (from source 15 via filter assembly 17 and fiber optics cable 33), via internal fundus retinal imager optics (not shown). Such illumination is reflected off the various layers of the retina, as illustrated in FIG. 6A, through beam splitter 49 (which has wavelength sensitive coatings to reflect beam 45 and to pass all of the light from source 15) and onto the surface of beam splitter 63. The wavefront from the retina is then directed to deformable surface 65 (where the conjugate wavefront is applied to correct for low order aberrations), reflected back through beam splitter 63, through imaging lens 69 and focused onto focal plane 61 (which is also the image plane of high resolution detector 25). Image data from detector 25 is transferred to computer 27 via data line 117 and data interface 115 which, in this case, includes an IEEE 1394 driver. Image data is transferred to memory 107 via subroutine 113, (which reformats the data, adds headers, and synchronizes the simultaneous collection of the Hartmannogram and high resolution detector data). Image data is also sent to monitor 29, via high resolution image processor 119 and data line 99, for screen display. As illustrated in FIG. 8 an acquisition window displays the most recent high-resolution image 121 from detector 25. This can be displayed along with the alignment window live video image 123 from detector 95. Main program software can also provide a series of previously taken high resolution images 125 of the retina.

Figure 9:
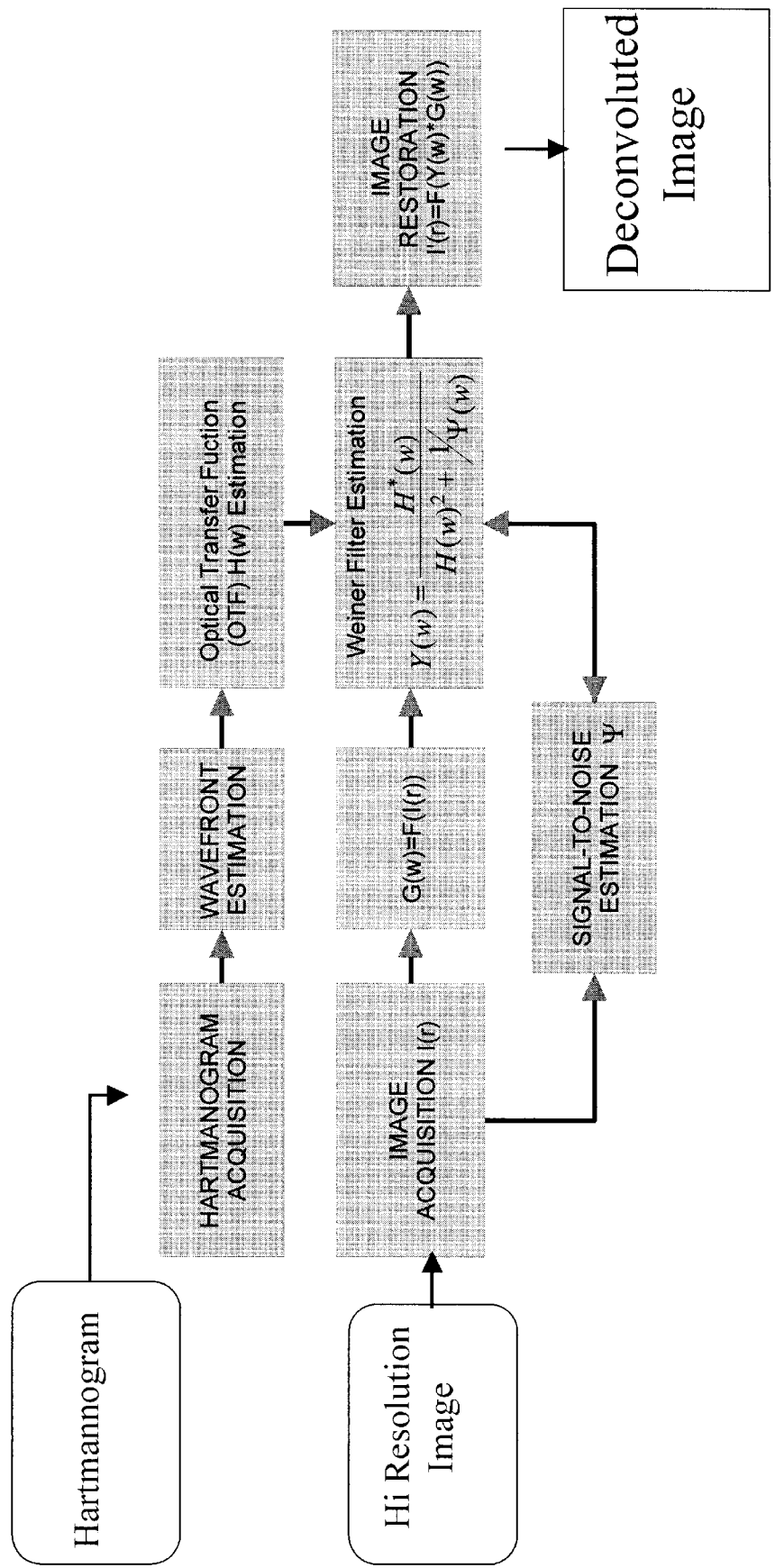
FIG. 9 is a flow diagram illustrating the algorithms used for the deconvolution and the image reconstruction of the present invention.
Figure 10:
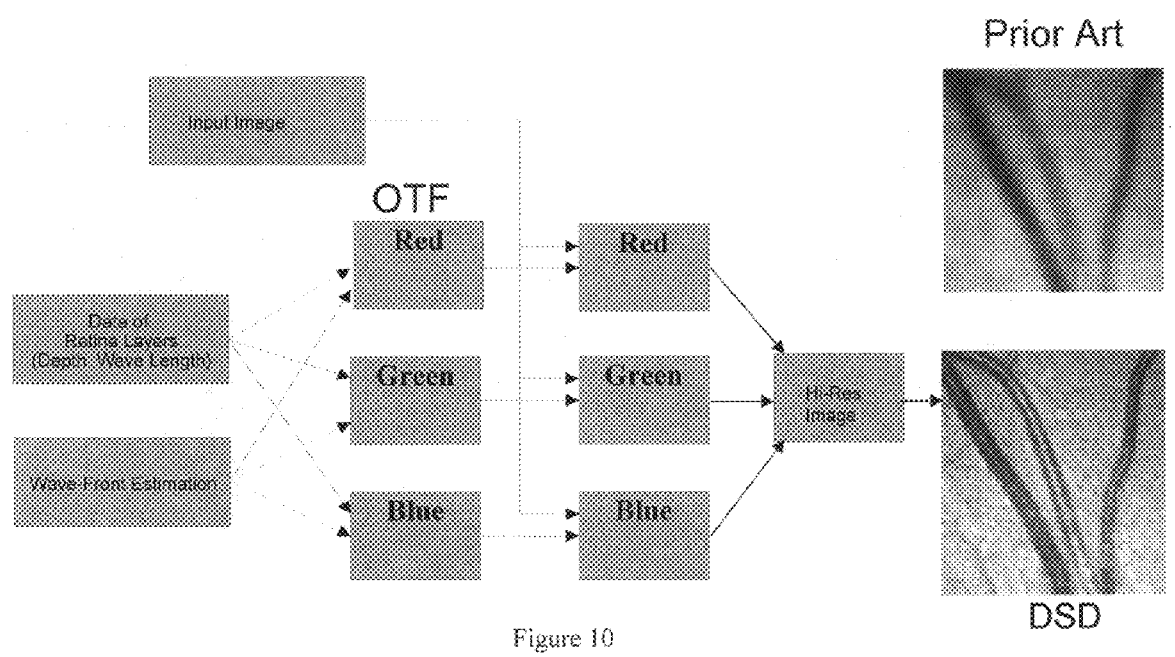
FIG. 10 is a flow diagram illustrating the application of the color-depth sensitive deconvolution algorithms for three wavelengths of light to produce color, depth sensitive deconvolution.

The deconvolution of the high-resolution images, via high resolution image processor 119, from detector 25 and the multispectral application of this technique is illustrated in FIGS. 9 and 10. Adaptive optics mirror 67 is very good at correcting low order aberrations. However, for higher order aberrations it is less effective. See Table 2 of A. Kudryashov et al., "Bimorph Mirrors for Correction and Formation of Laser Beams," where the RMS error for cornea and spherical aberrations is considerably higher than that for either defocus or astigmatism. To correct for higher order aberrations a deconvolution algorithm is used. See J. Primot et al., "Deconvolution from wave aberrations of the human eye using a Hartmann Shack wavefront sensor", JOAS A 7 1598–1608, 1990. The retinal image deconvolution of the present invention to correct for higher order aberrations is based on the simultaneous acquisition of two images of the human eye. One is the high-resolution retinal image 121 taken by high resolution CCD detector 25, partially corrected by bimorph mirror 67 (as explained above). The second image is the Hartmannogram from lenslet array 51. As discussed above, laser 41 (which is, for example, a low power semi-conductor laser) is used as the reference source for the Hartmannogram. Dithered reference source 19 forms a small, diffraction limited spot on the back of the retina, which sport serves as the reference point source for the wavefront measurements. Subroutine 103 reconstructs the information about wavefront distortions based on the analysis of the Hartmannogram. This information about the wavefront is presented as a set of Zernike aberration coefficients (36 in this application). From the wavefront shape the Optical Transfer Function (OTF), $H(\omega)$, of the eye is calculated. With further reference to FIG. 9, the high-resolution image from CCD detector 25 is expressed as a function of its intensity distribution, $I(r)$. $F(I(r))$ is the spatial Fourier transformation of $I(r)$, $G(\omega)$ is the Fourier spectrum of the high resolution image, and r and $\omega$ are the transversal coordinates in the spatial and frequency domains. From the OTF, $H(\omega)$, $G(\omega)$ and the signal-to-noise estimation $\psi$, a Weiner Filter Estimation is performed on the retinal image to correct for the high order aberrations (in an iterative process) and, thus, restore small image details of the retina. In this estimation $\psi(\omega)$ is the spectral power of the noise, and $Y(\omega)$ is the Wiener Filter Function.

The retina is a complex structure. From the optical point of view it is manifested in different effective reflection depths, depending on the wavelength. FIG. 6A illustrates these layers of the retina and from which layers various wavelengths of light are reflected. The wavelength of the reference source is taken into account in the calculation of the OTF. In addition to the deconvolution of the high resolution images and image reconstruction (as discussed above), the present invention is able to obtain multispectral images of the retina. This is achieved through the use of filters 17, the selection of which is controlled by computer 27, via control line 18, and the decomposition of the polychromatic OTF into three monochromatic OTFs for pre-selected wavelengths representing the primary RGB colors, as illustrated in FIG. 10. The monochromatic OTFs are determined by high resolution image processor 119 from the wavefront estimation discussed above, and data related to the retinal layers (i.e., depth and wavelength). Then, for each of the monochromatic OTFs, the correcting factor is calculated depending on the wavelength and effective depth of reflection. Deconvolution for each of the color channels of retinal image is carried out using corresponding OTF $G(\omega)$ and a Weiner Filter Estimation. Finally a full RGB image is assembled by superimposing each of the separately corrected images. FIG. 6A illustrates the layers of retina, and FIG. 6B the additional corresponding OTFs. Calculating the OTFs based on the use of the information on the human eye structure (information on depth of the retina layers depending on the reflected light wave-lengths) permits restoring of colored retinal images without any additional optical measurements. The depth sensitive deconvolution, DSD, algorithm as described in "Depth sensitive adaptive deconvolution of retinal Images", A.Larichev, N.Irochnikov and A.Kudryashov, 158–169, EBiOS200 Conference on Controlling Tissue Optical Properties, SPIE Proceedings 4162, Jul. 5–6, 2000, Technical Program, p.10, consists of three parallel-applied processes, each of them is analogous to the one described above. (See FIG. 14) All three share the information on wave-front aberrations, which in combination with the retina layer data permits carrying out deconvolution for every color subsets of the input picture data. Then three monochrome pictures combine in color one, which has much higher quality than the picture, obtained by the conventional algorithms.

FIG. 11 is a table comparing the features of achieved by the present invention by the present invention with the prior art. In all cases the features of instrument 11 represent an improvement.

Whereas the drawings and accompanying description have shown and described the preferred embodiment of the present invention, it should be apparent to those skilled in the art that various changes may be made in the form of the invention without affecting the scope thereof.

What we claim is:

1. An ophthalmic instrument comprising:
   (a) a retinal imager, said imager including optics for illuminating and imaging the retina of the eye;
   (b) means for generating a reference beam, said generating means being optically coupled to said imager optics to form a reference spot on said retina;
   (c) a wavefront sensor optically coupled to said imager optics for measuring the wavefront produced by optical aberrations within said eye and said imager optics;
   (d) first wavefront compensation means optically coupled to said imager optics for correcting large, low order aberrations in said wavefront;
   (e) a high resolution detector optically coupled to said imager optics and said first wavefront compensation means; and
   (f) computer means, said computer means connected to
      (i) said wavefront sensor,
      (ii) said first wavefront compensation means, and
      (iii) said high resolution camera,
   said computer means including second wavefront compensation means for correcting, small, high order aberrations.

2. The instrument of claim 1, wherein said wavefront sensor includes a Shack-Hartmann wavefront sensor having a lenslet array and a detector positioned in the front surface of said lenslet array, in operation said wavefront sensor producing a Hartmannogram which is transmitted to said computer means.

3. The instrument of claim 2, wherein said computer includes means for estimating said wavefront from said Hartmannogram and sending a correction signal to said first wavefront compensation means to correct large, low order aberrations in said wavefront.

4. The instrument of claim 3, wherein said means for estimating said wavefront requires only one said Hartmannogram, thereby reducing the exposure of said retina to said spot, and avoiding the need to register successive Hartmannograms.

5. The instrument of claim 1, wherein said first wavefront compensation means includes a deformable mirror.

6. The instrument of claim 5, wherein said deformable mirror is a bimoph mirror.

7. The instrument of claim 1, wherein said second wavefront compensation means includes deconvolution algorithm means, said deconvolution algorithm means utilizing information from both said wavefront sensor and said high resolution detector.

8. The instrument of claim 7, wherein said deconvolution algorithm means includes means to correct residual low order aberrations not corrected by said first wavefront compesation means.

9. The instrument of claim 7, wherein said computer means includes means for acquiring images from said high resolution detector.

10. The instrument of claim 9, wherein said wavefront sensor includes means for producing Hartmannograms which are transmitted to said computer means.

11. The instrument of claim 10, wherein said deconvolution algorithm means includes means for estimating the wavefront sensed by said wavefront sensor, means for estimating the Optical Transfer Function of said wavefront, and Weiner Filter Estimation means.

12. The instrument of claim 11, wherein said deconvolution algorithm means includes image reconstruction algorithm means.

13. The instrument of claim 12, wherein said retinal imager includes a source for illuminating said retina.

14. The instrument of claim 13, further including a plurality of optical filters and means for selectively positioning any one of said filters between said source and said imager optics, whereby said retina may be illuminated by light of a preselected wavelength.

15. The instrument of claim 14, wherein said deconvolution algorithm includes means for accounting for the reflectance of various wavelengths of light from different depths within said retina to produce a multispectral deconvoluted image of said retina.

16. The instrument of claim 1, further including a means for dithering said reference beam.

17. The instrument of claim 16, wherein said means for generating a reference beam as a laser.

18. The instrument of claim 16, wherein said means for dithering is a rotatable wedge.

19. The instrument of claim 1, further includes means for producing a wide field of view.

20. The instrument of claim 19, wherein said means for producing a wide field of view has a field of view of, up to, 20 degrees.

21. The instrument of claim 19, wherein said high resolution detector is a large format, high resolution detector.

22. The instrument of claim 1, wherein said retinal imager is a fundus imager.

23. An ophthalmic instrument comprising:
   (a) a retinal imager, said imager including optics of illuminating and imaging the retina of the eye;
   (b) means for generating a reference beam for placing a reference area on said retina;
   (c) a wavefront sensor coupled to said imager optics for measuring the wavefront generated by the optical aberrations within said eye and said imager optics;
   (d) wavefront compensation means coupled to said imager optics for correcting aberrations; and
   (e) means for dithering said reference beam.

24. An ophthalmic instrument comprising:
   (a) a retinal imager, said retinal imager including optics for illuminating and imaging the retina of the eye;
   (b) means for generating a reference beam, said generating means being optically coupled to said imager optics to form a reference area on said retina;
   (c) a wavefront sensor coupled to said imager optics for measuring the optical aberrations within said eye and said imager optics;
   (d) a high resolution detector optically coupled to said imager optics and said first wavefront compensation means; and
   (e) computer means, said computer means connected to
      (i) said wavefront sensor,
      (ii) said first wavefront compensation means, and
      (iii) said high resolution camera,
   said computer means including wavefront compensation means.

25. The instrument of claim 24, wherein said wavefront compensation means includes deconvolution algorithm means, said deconvolution algorithm means utilizing information from both said wavefront sensor and said high resolution detector.

26. The instrument of claim 25, wherein said computer means includes means for acquiring images from said high resolution detector.

27. The instrument of claim 26, wherein said wavefront sensor includes means for producing Hartmannograms which are transmitted to said computer means.

28. The instrument of claim 27, wherein said deconvolution algorithm means includes means for estimating the wavefront sensed by said wavefront sensor, means for estimating the Optical Transfer Function of said wavefront, Weiner Filter Estimation means, and image reconstruction algorithm means.

29. The instrument of claim 28, wherein said retinal imager includes a source for illuminating said retina.

30. The instrument of claim 29, further including a plurality of optical filters and means for selectively positioning any one of said filters between said source and said imager optics, whereby said retina may be illuminated by light of a preselected wavelength.

31. The instrument of claim 30, wherein said deconvolution algorithm includes means for accounting for the reflectance of various wavelengths of light from different depths within said retina to produce a multispectral deconvoluted image of said retina.

32. An adaptive optics device for use in association with a fundus retinal imager, said fundus imager including optics for illuminating and imaging the retina of the eye, said device comprising:
  (a) a wavefront sensor optically coupleable to said fundus retinal imager optics, for measuring the wavefront produced by optical aberrations within said eye and said fundus retinal imager optics;
  (b) first wavefront compensation means, optically coupleable to said fundus optics, for correcting large, low order aberrations in said wavefront;
  (c) a high resolution detector optically coupleable to said fundus optics; and
  (d) and said first wavefront compensation means; and
  (e) computer means, said computer means connected to
    (i) said wavefront sensor,
    (ii) said first wavefront compensation means, and
    (iii) said high resolution camera,
said computer means including second wavefront compensation means for correcting small, high order aberrations.

* * * * *